United States Patent [19]
Thiele et al.

[11] 4,172,128
[45] Oct. 23, 1979

[54] PROCESS OF DEGRADING AND REGENERATING BONE AND TOOTH MATERIAL AND PRODUCTS

[76] Inventors: Heinrich Thiele, Neue Universitaet, Kiel; Erhard Thiele, Reventlow-Allee 9, 23 Kiel, both of Fed. Rep. of Germany

[21] Appl. No.: 796,122

[22] Filed: May 12, 1977

Related U.S. Application Data

[63] Continuation of Ser. No. 574,648, May 5, 1975, abandoned, which is a continuation of Ser. No. 344,577, Mar. 26, 1975, abandoned, which is a continuation of Ser. No. 57,332, Jul. 22, 1970, abandoned, which is a continuation-in-part of Ser. No. 583,989, Oct. 3, 1966, abandoned.

[51] Int. Cl.² ............................................. A61K 35/32
[52] U.S. Cl. ...................................... 424/95; 32/10 A

[58] Field of Search ................ 424/95; 32/DIG. 10 A

[56] References Cited
U.S. PATENT DOCUMENTS
2,968,593  1/1961  Rapkin .................................. 424/95

*Primary Examiner*—V. D. Turner

[57] ABSTRACT

Regenerated and reconstructed bone and tooth material which is well tolerated by the body and can be implanted without any danger of rejection is obtained by first demineralizing natural bone or tooth material obtained, for instance, from animals, converting said demineralized material into a mucopolysaccharide-free colloidal solution, adding to said solution a physiologically inert foreign mucopolysaccharide, gelling said solution, and remineralizing the resulting gel.

11 Claims, No Drawings

4,172,128

PROCESS OF DEGRADING AND REGENERATING BONE AND TOOTH MATERIAL AND PRODUCTS

CROSS-REFERENCE TO RELATED APPLICATION

The present application is a continuation of application Ser. No. 574,648, filed on May 5, 1975 which, in turn, is a continuation of application Ser. No. 344,577, filed on Mar. 26, 1973 as a continuation of application Ser. No. 57,332, filed July 22, 1970, the last named application being a continuation-in-part of application Ser. No. 583,989, filed on Oct. 3, 1966, said earlier applications Ser. Nos. 574,648; 344,577; 57,332; and 583,989 being now abandoned.

BACKGROUND OF THE INVENTION (1) Field of the Invention

The present invention relates to a process of reconstructing and regenerating bone and tooth material and more particularly to a process of producing artificial bone and tooth material which is useful in surgery and dentistry and which is similar in its structure and composition to natural bones and teeth, and to products obtained by said process.

(2) Description of the Prior Art

As is known, bones and teeth are composed of a matrix of organic material consisting of collagenous fibrils and a binding substance of mucopolysaccharides as well as of the inorganic component, namely calcium phosphate in the form of hydroxy apatite. The organic matrix is formed by filiform molecules arranged parallel to each other. Furthermore, the tissue is traversed by numerous microscopic capillaries which are oriented vertically to said filiform molecules.

It is known to subject animal bones to a treatment so that they can be transplanted to other living animal bodies and also to human beings without substantial deleterious effects. For this purpose the animal bone material is maintained in a refrigerated state in a bath containing an antibacterial or antifungal agent and a blood component from the same species animal from which the bone material is derived, such as blood plasma or blood serum. The thus preserved bone material can be used for splints, bridging elements, or grafts. It can furthermore be removed from the organic liquid and pulverized. The pulverized bone is then blended with plasma clotting substance as a binder to yield a paste. This bone powder paste is useful as bed or filler between the bone sections to be grafted and also in dentistry as a filler for dental cavities and the like. It was found, however, that fequently grafts of bone material preserved in this manner were rejected by the body.

RAPKIN in U.S. Pat. No. 2,968,593 describes a method of preparing inorganic bone material by heating animal bone material in a liquid to a temperature from about 80° C. to about 100° C., drying the heated bone material, substantially defattening it with a fat extracting solvent, and removing the organic matrix from the defattened bone material, for instance, by extraction with ethylene diamine to obtain the inorganic matrix. Such an inorganic bone material which is free of organic matter is used for transplantation from an animal of one species to another species without any adverse effect. However, due to the absence of the organic matrix the inorganic bone material is of relatively low strength and difficult to handle.

SUMMARY OF THE INVENTION

It is one object of the present invention to provide a novel process of producing bone material useful for reconstructing and regenerating bones and teeth, said bone material being readily accepted by the body and corresponding in its composition and structure to natural bones and teeth.

Another object of the present invention is to provide such novel and valuable bone and tooth material useful in the reconstruction and regeneration of natural bones and teeth.

Other objects of the present invention and advantageous features thereof will become apparent as the description proceeds.

In principle the process according to the present invention comprises the following steps:

(a) The coarsely ground bone or tooth material is demineralized by treating the same with an aqueous solution of a demineralizing agent under conditions whereby the bone or tooth collagen remains substantially uaffected.

(b) The demineralized organic matrix of bone or tooth material is treated with an agent causing swelling of the collagen and dissolving of the mucopolysaccharides.

(c) The dissolved mucopolysaccharides are removed from said swollen material.

(d) The swollen demineralized bone or tooth material is dissolved in a solvent thereby forming a colloidal solution of the organic matrix.

(e) To the resulting mucopolysaccharide-free colloidal solution there is added a physiologically inert foreign mucopolysaccharide or polyuronic acid in an amount sufficient to cause orientation on subsequent gel formation.

(f) Hydrogen ions or polyvalent metal ions are caused to diffuse into said colloidal solution to form a gel of oriented filiform collagen molecules with capillaries extending therethrough.

These process steps permit to reversibly reconstruct and regenerate the organic matrix of the osteons in bones and teeth.

(g) If desired, the resulting gel is partly or completely remineralized to yield the reconstructed bone or tooth material.

The above given steps are preferably carried out as follows:

Step (a): Demineralization, i.e. decalcification must be carried out so carefully that the organic matrix and especially the collagen thereof is not destroyed or unfavorably affected. For this purpose the bone and tooth material is subjected to an electrophoretic treatment preferably in dilute mineral acid or to the action of chelating agents or of complex compound-forming acids such as citric acid, lactic acid, or hypophosphorous acid $H_3PO_2$.

After such a demineralization treatment the collagen framework or matrix of the bone or tooth material is obtained in a highly purified form and substantially free of mineral matter and other undesired accompanying substances.

Demineralization of the tooth enamel requires more time than that of bone material or the dentine.

Preferably the demineralized material is carefully washed with distilled water until free of acid.

Step (b): The resulting calcium- and mineral-free matrix is then treated with a swelling agent and thus converted into the swollen state. Preferably swelling is achieved by a treatment with an alkaline solution, preferably with dilute sodium hydroxide solution or lithium hydroxide solution. Such alkaline solutions dissolve the mucopolysaccharides which can be removed by decanting. Solutions of salts or acids may also be employed for causing swelling of the matrix.

Step (c): The mucopolysaccharides are separated therefrom yielding a collagen sol ready for reconstitution.

Step (d): The resulting swollen matrix is then dissolved to a sol. Sol formation is achieved by the addition of further amounts of alkaline agents or of acids. Vigorous stirring is essential for causing complete homogenization of the sol.

Removal of excess alkaline agent, residual inorganic and organic materials from the sol is achieved by dialysis or electrodialysis against distilled water. The resulting purified collagen sol is highly susceptible to bacterial decomposition. Therefore, further processing should take place under sterile conditions in closed, cooled, sterile reaction vessels. After dialysis or electrodialysis, a clear, highly viscous, colorless, somewhat ropy or stringy sol of flat or insipid taste and smelling like living matter remains. Elementary collagen fibrils are discernible under the electron microscope.

Step (e): Physiologically inert foreign mucopolysaccharides and/or polyuronic acids are admixed to said sol and dissolved therein in a predetermined amount as ascertained by preliminary tests. These preliminary tests are carried out with varying proportions of protein to mucopolysaccharides in order to determine the mucopolysaccharide addition required to achieve optimum results on reconstruction and regeneration of the bones or teeth. A preferred quotient of mucopolysaccharide to protein is about 0.7. The type of mucopolysaccharide added may also vary. Furthermore, procollagen, profibrin, and/or elastin may also be added to the sol to impart to the reconstituted bone or tooth product the desired properties.

The suitable quotient "mucopolysaccharide to protein" is determined, for instance, by adding to the protein sol increasing amounts of mucopolysaccharide and/or polyuronic acid and determining its viscosity. A curve is plotted point by point from the viscosity values found. The maximum of said curve corresponds to the quotient determined according to the viscosity method.

Step (f): The resulting clear viscous so-called "symplex" sol containing the collagen and the mucopolysaccharide and/or polyuronic acid is preferably poured in the form of a thin layer over the surface of a porous mold of the desired shape and the thus coated mold is immersed into a suitable electrolyte to produce a thin membrane of the solidified gel. The remaining sol is gradually and continuously introduced into the mold while it is immersed in an electrolyte so that the ionotropic gel is formed gradually and continuously. This gel corresponds to the original matrix.

The term "symplex" designates salts of a polymer anion with a polymer cation or amphiion. Such a symplex sol of collagen and mucopolysaccharide can be ionotropically oriented by allowing ions to diffuse thereinto, thus causing orientation and fixation of the latter to an ionotropic gel which has the desired macroscopic and microscopic properties and represents the organic matrix of the reconstituted bone or tooth.

The electrolyte supplying the gel-forming ions may be a dilute organic acid such as lactic acid or citric acid. Metal salts may also be used for gel formation. The preferred metal ions are those of polyvalent metals such as copper, cadmium, lead, zinc, calcium, aluminum, lanthanum, and others which are preferably supplied in the form of their nitrates, chlorides, bromides, sulfates, or acetates, preferably in the form of N solutions. Once the final structure of the gel is formed, the metal ions can be exchanged by hydrogen ions without any substantial change in the structure and orientation of the gel. Only very small ion concentrations, comparable to those of trace elements, are necessary for gel formation.

During gel formation there are also formed, vertically to the filamentary molecules, numerous substantially straight, parallel capillaries of circular cross-section. Thus the thin membrane formed on the surface of the mold as well as the resulting gel remain permeable to the gel-forming ions so that the sol continuously added is also solidified to the desired ionotropic gel.

The shape of the gel is determined, of course, by the respective shape of the porous mold and may be the shape of the bone or part of a bone or tooth to be implanted.

If desired, the resulting gel may be cross-linked and rendered insoluble, for instance, by impregnating the gel with a polymerizable monomer such as a methacrylic acid ester, a mixture of urea and formaldehyde, styrene, a polyester and a polyisocyanate, and others. Thereafter, excess monomer is removed from the capillaries in the gel, for instance, by dissolving out the monomer. The monomer may contain polymerization catalysts such as an organic peroxide, for instance, benzoyl peroxide. The monomeric material remaining in the capillaries is polymerized by the action of heat or, when using polymerization accelerators, on standing. Care must be taken that the capillaries are not completely filled with the polymer and/or cross-linking agent but that the gel still remains porous and permeable to ions. Of course, if the reconstituted bone and tooth material is used for implantation in the human body, no such cross-linking and insolubilization is required, although a certain degree of cross-linking may be desired to strengthen the matrix. Treatment with formaldehyde or tannic acid may also cause such strengthening of the gel matrix.

Gradual and continuous introduction of the sol into the mold is necessary in order to counteract the shrinkage due to the orientation of the collagen fibrils and bundles of fibrils. As a result thereof, the fibrils arrange themselves more tightly parallel to each other and form the matrix structure.

In addition to such a primary shrinkage, a secondary shrinking of the gel is observed when allowing the matrix to remain in contact with the electrolyte solution after gellation and growth are completed. This secondary shrinkage achieves further orientation, compaction, and consolidation of the matrix. Such secondary shrinkage proceeds continuously and can be intensified by the use of concentrated electrolytes, or, preferably, by alternately exposing the gel to hydrogen and metal ions.

Both types of shrinkage are manifestations of a progressive orientation and dehydration of the gel which is accompanied by progressive solidification and strengthening of the matrix. The degree of dehydration can readily be varied by interrupting secondary shrinkage after a predetermined period of time.

The addition of physiologically inert foreign mucopolysaccharides or polyuronic acids to the collagen sol before gellation is of importance with respect to the formation of the desired ionotropic structure of the gel. Pure collagen sols yield only slightly ionotropic gels. But even small amounts of mucopolysaccharides or polyuronic acids produced pronounced ionotropic effects. Thus, for instance, addition of chondroitin sulfuric acid causes extensive formation of capillaries while hyaluronic acid is more particularly responsible for spatial cross-linking. The preferred orienting agent is alginic acid and its salts. Addition of these mucopolysaccharides results in strong orientation which is characterized by the birefringence of the gel.

Step (g): The gel is finally remineralized, if desired, to yield the reconstructed bone or tooth material.

Mineralization is effected by exposing the gel alternately and repeatedly to the action of calcium ions and phosphate ions. Thereby, preferably, the ionic groups of the mucopolysaccharides are first charged with calcium and the excess of calcium ions is removed by washing. Thereafter calcium phosphate is allowed to crystallize between the capillaries and therewithin whereby in the case of bone material and dentine intercapillary mineralization is effected while for preparing tooth enamel intercapillary as well as intracapillary mineralization is achieved. Enzymatic mineralization may also be employed.

Preferably an acid phosphoric acid solution saturated with di-calcium phosphate and an alkaline calcium phosphate solution are allowed to act alternately upon the reconstituted matrix gel. On alternately allowing both solutions to act four times upon the gel, remineralization of the matrix is achieved to between 30% and 40%.

DESCRIPTION OF THE PREFERRED EMBODIMENTS

The following examples serve to illustrate the present invention without, however, limiting the same thereto.

EXAMPLE 1

Teeth of cattle are cleansed by means of dental claw-like instruments or chisels to remove concretions adhering thereto. The tooth material is further cleansed with pumice and water by means of rotating brushes and is crushed and ground to pieces of a diameter of about 1 mm. to 3 mm.

Should it become necessary to store the crushed tooth material, if it cannot be worked up immediately, it is preferably placed into a mixture of glycerol and water (1:1) and kept at a temperature of about 4° C. Before further working up such stored tooth material, it is repeatedly washed with distilled water.

Demineralization of the thus cleaned tooth material is carried out by gently stirring 100 g. thereof in 400 cc. of hypophosphorous acid $H_3PO_2$. Said acid dissolves the calcium phosphate. The mixture of tooth material and acid is kept at about 20° C. and the acid is replaced every 5 hours. Replacement of the acid is repeated until incineration tests show that all of the calcium phosphate has been dissolved and removed from the tooth material. The remaining collagen matrix or framework of the tooth material is substantially free of mineral material. It is washed in a fine-meshed screening or sifting container which is immersed into a vessel with distilled water or is suspended on the axial shaft of a vibrator. Washing of the demineralized tooth material to remove excess acid and salts is completed at 20° C. within about 30 hours.

The resulting dentine collagen matrix is caused to swell by stirring it gently with 400 cc. of 2 N sodium hydroxide solution at 15° C. for 200 hours. Excess sodium hydroxide solution is removed by decanting, whereby the dissolved mucopolysaccharides are also removed.

The swollen matrix is then dissolved by vigorous stirring in 2 N sodium hydroxide solution. The resulting sol is immediately dialyzed at 15° C. against distilled water in an oblique cylindrical dialyzer until neutral whereby care is taken that sterile conditions are maintained during dialysis. After about 40 hours the distilled water is of neutral reaction and excess alkali hydroxide and salts are removed from the sol. After homogenization, the dry content of the sol is determined and the quotient protein to mucopolysaccharide is calculated. The resulting sol contains the protein of the dentine. The sol is clear, highly viscous, somewhat stringy, colorless, of insipid taste and the smell of living matter. Elementary collagen fibrils are discernible under the electron microscope.

The resulting clear, viscous symplex sol is poured over the surface of a porous mold of the desired shape to form a thin coating thereon and the mold is immersed into an 0.4 N citric acid solution. Diffusion of the hydrogen ions of said acid solution through the porous mold causes formation of a thin membrane which is extended between two annular gaskets. Into this membrane there is introduced continuously and gradually the symplex sol while the mold is immersed in said electrolyte solution. Diffusion of the hydrogen ions through the mold, the porous membrane, and the resulting gel gradually builds up the gel whereby the collagen fibrils and bundles of fibrils are oriented and form the desired ionotropic gel structure. Thereby, the shrinkage which takes place due to the compaction of the tightly arranged and oriented collagen fibrils and to their partial dehydration, is compensated for by the continuous addition of the symplex sol to the gel already formed in the mold.

Thereafter, the resulting gel is remineralized by a repeated alternate treatment with a soluble calcium salt replacing the hydrogen ions in the mucopolysaccharides, followed by removing excess calcium ions by washing, and a subsequent treatment with an acid calcium phosphate solution whereby calcium phosphate percipitates and crystallizes within the capillaries of the ionotropic gel.

The recalcified tooth material corresponds to the natural dentine. When produced in a mold shaped like a tooth, an artificial tooth is produced which can be implanted into the jaw bone. It is well tolerated by the human body and, in contrast to other implanted teeth of artificial nature, is readily incorporated into the body and not rejected by it. In fact, the remineralized ionotropic gel according to the present invention supplies the building material to the place where a defect is to be repaired. Since the reconstructed tooth material corresponds in its composition and structure to the missing tooth material, it is not rejected as a foreign body but is readily accepted by the body.

The remineralized gel is stored before use in sterilized plastic bags filled with Ringer's solution or with Krebs' solution.

EXAMPLE 2

Demineralization of the crushed and cleaned tooth material can also be carried out as follows:

100 g. of the tooth material are placed into the middle chamber of a three-chamber electrodialysis cell. A mixture of dilute hydrochloric acid and formic acid is also introduced into said cell. Distilled water is continuously passed through the outer cathode and anode chambers. On application of an electrical current to the cathode and anode, the initial voltage of 4 Volt increases to about 50 Volt at the end of the demineralization process. The temperature is kept below 40° C. The resulting demineralized matrix is further worked up as described in Example 1.

EXAMPLE 3

The procedure is the same as described in Example 1 whereby, however, the bones of calves are used as starting materials and demineralization is effected by the action of 0.1 N citric acid.

Other hydroxy carboxylic acids and also keto carboxylic acids such as 0.1 N to 4.0 N lactic acid, malic acid, tartaric acid, pyruvic acid, and others can also be used.

EXAMPLE 4

The procedure is the same as described in Example 1 whereby, however, the bones of pigs are used as starting material and demineralization is effected by the action of N acetic acid.

Other organic acids such as 0.1 N to 4.0 N formic acid, and others can also be used.

EXAMPLE 5

The procedure is the same as described in Example 1 whereby, however, the bones of cattle are used as starting material and demineralization is effected by the action of N phosphoric acid. 0.1 N to 3 N phosphorous acid can also be used.

EXAMPLE 6

The procedure is the same as described in Example 1 whereby, however, the bones of sheep are used as starting material and demineralization is effected by treating the bones repeatedly with 0.1 N hydrochloric acid at 20°–40° C. while gently stirring the demineralization mixture and decanting and replacing the decanted acid every 12 hours.

In place of hydrochloric acid, there can be used other mineral acids such as 0.1 N to 2.0 N hydrobromic acid, nitric acid and others.

EXAMPLE 7

The procedure is the same as described in Example 1 whereby, however, the bones of cattle are treated with an N aqueous solution of ethylene diamine tetraacetate.

Other chelating agents such as nitrilotriacetic acid, di-ethylene triamine penta-acetic acid can also be used in concentrations of 0.1 normality to saturated solutions. If desired, these chelating agents can be used together with hydroxy carboxylic acids such as citric acid, oxalic acid, gluconic acid, and others.

EXAMPLE 8

Demineralization by electrodialysis is carried out by placing coarsely comminuted bones of cattle and 0.5 N nitric acid into a porcelain container and the mixture is electrodialyzed by applying thereto a direct current voltage between 2 volts and 50 volts using platinum electrodes and gently stirring the solution to be dialyzed at room temperature.

It is, of course, understood that any demineralizing agent may be used to dissolve the calcium phosphate from the bone or tooth material provided that said agent does not substantially denature or irreversibly change the organic matrix of said bone or tooth material.

EXAMPLE 9

The procedure is the same as described in Examples 1 to 8 whereby, however, swelling of the demineralized bone or tooth matrix is effected by gently stirring the demineralized particles of bone or tooth material in N lithium hydroxide solution at 4° C. Thereby the mucopolysaccharides, the proteins of medium molecular weight such as the albumins and the globulins and especially the strongly antigenic γ-globulins and the amino acids are dissolved. The lithium hydroxide solution is decanted and replaced by fresh solution twice daily until the above mentioned components are completely eliminated. At the same time all the cells present in the organic bone or tooth matrix are plasmolyzed and the cell components are set free and are dissolved. Removal of the mucopolysaccharides and other cell components is preferably carried out by treating the organic matrix with alkaline agents and be repeatedly decanting the swelling fluid. Centrifuging or filtering do not yield as good results as decanting.

EXAMPLE 10

The procedure is the same as described in Examples 1 to 8 whereby, however, swelling of the demineralized bone or tooth matrix is effected by gently stirring the demineralized particles of bone or tooth material in 2 N potassium hydroxide solution at a temperature between 4° C. and 20° C. The mucopolysaccharides and other cell components are removed by repeatedly decanting and replacing the potassium hydroxide solution.

EXAMPLE 11

The procedure is the same as described in Examples 1 to 8 whereby, however, swelling of the demineralized bone or tooth matrix is effected by gently stirring the demineralized particles of bone or tooth material in 0.1 N calcium hydroxide solution. The mucopolysaccharides and other cell components are removed by repeatedly decanting and replacing the calcium hydroxide solution.

EXAMPLE 12

The procedure is the same as described in Examples 1 to 8 whereby, however, swelling of the demineralized bone or tooth matrix is effected by gently stirring the demineralized particles of bone or tooth material in 20% urea solution. The mucopolysaccharides and other cell components are removed by repeatedly decanting and replacing the urea solution.

EXAMPLE 13

The procedure is the same as described in Examples 1 to 8 whereby, however, swelling of the demineralized bone or tooth matrix is effected by gently stirring the demineralized particles of bone or tooth material in 10% tetraethylene pentamine solution. The mucopolysaccharides and other cell component are removed by repeatedly decanting and replacing the tetraethylene pentamine solution.

In place of urea and tetraethylene pentamine there can be used, as swelling agents, water soluble urea derivatives such as urethane or other aliphatic polyamines and amines such as methylamine, dimethylamine, ethylene diamine, ethylamine, and others, or other agents which are capable of splitting up hydrogen and sulfur bridges, for instance; salts such as sodium chloride and salts with hydrotropic activity, for instance, lithium rhodanide, zinc chloride, and others, or acids such as phosphoric acid, formic acid, or hydroxy carboxylic acids, for instance, lactic acid, or sulfur containing compounds, such as dimethylsulfoxide, dimethyl formamide, and others. The preferred swelling agents are lithium and sodium hydroxide. They and other alkaline agents dissolve the mucopolysaccharides and thus effect simultaneous swelling and removal of the dissolved mucopolysaccharides by decanting.

EXAMPLE 14

The procedure is the same as described in preceding Example 1 to 13 whereby, however, dissolution of the swollen particles of bone or tooth material is achieved by placing said particles into an aqueous 50% urea solution and subjecting the mixture to the action of a homogenizer.

EXAMPLE 15

The procedure is the same as described in Example 1 whereby, after decanting the sodium hydroxide solution, fresh 2 N sodium hydroxide solution is added to the swollen material. The mixture is pressed through the narrow gap formed by the movement of a piston in a cylinder wherein the swollen material is placed, said piston being spaced from and not exactly fitting the cylinder wall. The resulting sol has a high viscosity, is thixotropic, and exhibits double fraction. It is diluted with the same volume of water.

Excess dissolving agent, i.e. sodium hydroxide, is removed, after decanting, by electrodialysis against water. Air bubbles which may be entrained in the sol, are removed by centrifuging the same.

EXAMPLE 15

The procedure is the same as described in Examples 1 to 14, whereby alginic acid is added to the sol to form the symplex sol and is dissolved therein, in place of chondoitrin sulfuric acid.

EXAMPLE 16

The procedure is the same as described in Examples 1 to 14, whereby pectinic acid is added to the sol to form the symplex sol and is dissolved therein, in place of chondoitrin sulfuric acid.

EXAMPLE 17

The procedure is the same as described in Examples 1 to 14, whereby carragheenin is added to the sol to form the symplex sol and is dissolved therein, in place of chondoitrin sulfuric acid.

Other mucopolysaccharides or polyuronic acids than chondoitrin sulfuric acid, alginic acid, pectinic acid, carragheenin as given in the preceding examples, such as hyaluronic acid, dermatan sulfuric acid, kerato sulfuric acid, pectic acid, pectins, chondrus acid, glucuronic acid, galacturonic acid, guaran phosphoric acid, and their water soluble salts as well as water soluble alginates and pectinates, and derivatives thereof such as their amino and acetyl derivatives can also be added to the sol of the organic bone or tooth matrix in order to cause ionotropic orientation of the filiform collagen molecules thereof on gel formation. Synthetic polycations such as polyacrylic acid, polymethacrylic acid, and others may also be used provided they are physiologically inert. Thereby, the acid groups of the mucopolysaccharides or polyuronic acids, i.e. their carboxyl and/or sulfonyl groups are bound by the proteins. The resulting symplex has the properties of a chemically unitary amphi-ion. Alginic acid, however, has proved to give best results.

As stated above, optimum symplex sols contain predetermined amounts of protein and mucopolysaccharide or polyuronic acid. Usually a ratio of proteins to mucopolysaccharide between about 96:4 and 65:35 and preferably between about 95:5 and 75:25 depending on the mucopolysaccharide or polyuronic acid used produces satisfactory gels on ion diffusion.

EXAMPLE 18

The procedure is the same as described in Examples 1 to 17 whereby, in place of the hydrogen ion supplying, gel forming 0.4 N citric acid solution, an aqueous N cupric nitrate solution is placed into the container into which the porous mold is partly immersed so that the gelling ions diffuse through the porous walls of the mold into the sol solution placed into the mold. As soon as the gradually produced gel has attained the desired shape, the cupric ions are exchanged against hydrogen ions by treating the mold with a dilute acetic acid solution. Excess hydrogen ions are finally removed from the shaped gel by dialysis of electrodialysis.

EXAMPLE 19

The procedure is the same as described in Examples 1 to 17 whereby, in place of the hydrogen ion supplying, gel forming 0.4 N citric acid solution, an aqueous 0.1 N cadmium sulfate solution is used to supply the gel-forming ions. The cadmium ions are removed by treating the mold with the gel with 0.1 N citric acid.

EXAMPLE 20

The procedure is the same as described in Examples 1 to 17 whereby, in place of the hydrogen ion supplying, gel forming 0.4 N citric acid solution, an aqueous 0.5 N calcium chloride solution is used to supply the gel-forming ions. Removal of the calcium ions and replacement by hydrogen ions is not necessary when subsequently mineralizing the reconstituted matrix structure.

EXAMPLE 21

The procedure is the same as described in Examples 1 to 17 whereby, in place of the hydrogen ion supplying, gel forming 0.4 citric acid solution, an aqueous 0.2 N aluminum nitrate solution is used to supply the gel-forming ions. The aluminum ions are removed by treating the mold with the gel with 0.1 N hydrochloric acid.

Orientation of the filamentary molecules by ion diffusion according to the present invention requires the selection of suitable compensating ions or "gegenions" (ions of opposite charge) which do not simply precipitate the filamentary molecules but which, at the same time, retain the oriented filamentary molecules in their gelled bond or association. Suitable salts are aluminum, chromium (III), lead (II), cadmium, copper (II), calcium salts, preferably their nitrates. In general, the gels produced with aluminum and chromium (III) ions are not very ductile and tend to crumble while those produced with calcium salts are relatively soft. The preferred ions are the cadmium and copper ions. Preferably 0.1 N to 0.5 N solutions of said salts are used whereby the dry substance content of the symplex sol is between about 0.3% to 1.0% and preferably between 0.5% and 0.75%.

It was found that the gels produced with metals of the transition series such as iron, nickel, cobalt, and the platinum metals, are gels with capillaries of a diameter of 0.5 mm. or less while those gels which are produced with aluminum and chromic ions usually do not possess such capillaries.

Gel formation may also be effected by a treatment with dilute mineral acids, such as 0.1 N hydrochloric acid. However, such a treatment has the disadvantage that the orientation of the filamentary molecules gradually decreases and that the gel slowly dissolves. Therefore, it is the preferred procedure either (a) to allow an acid to act on the sol while simultaneously cross-linking the filamentary molecules or
(b) to use acids the anions of which have a cross-linking effect.

Simultaneous treatment with an acid and a cross-linking agent is, for instance, achieved by using water-soluble cross-linking agents such as short-chain aldehydes, preferably formaldehyde, or $\alpha,\omega$-dialdehydes, such as glutar dialdehyde, 1-hydroxy adipic dialdehyde and the like compounds. For this purpose the sol is, for instance, covered by a layer of a mixture of 0.2 N hydrochloric acid and an 0.2% formaldehyde solution (1:1). The resulting gels are washed with water until excess formaldehyde is removed. The resulting gels show birefringence and are stable.

Treatment of the gels produced by the action of polyvalent metal ions, with acids and the above-mentioned cross-linking agents in order to exchange the metal ions by hydrogen ions is, of course, also possible.

Instead of using acids and cross-linking agents, the same gel-producing effect is achieved by means of acids the anions of which have a cross-linking effect. Such acids, for instance, are polybasic organic acids such as tartaric acid, malic acid, citric acid, and the like acids. These acids are capable of fixing the ionotropic gel structure for a prolonged period of time. Gel formation is achieved, for instance, by covering the sol with 0.1 N solutions of said acids.

Cross-linking, for instance, with formaldehyde may also be effected before treating the gel with acids in order to exchange the metal ions. For this purpose the gel is kept, for instance, at 4° C. in an 0.01% formaldehyde solution for at least 24 hours whereafter replacement of the metal ions by hydrogen ions is achieved by a treatment with 0.1 N hydrochloric acid without dissolving or destroying the gel.

It is, of course, also possible to treat the gel with polybasic organic acids, for instance, with citric acid solutions whereby not only the metal ions are exchanged by hydrogen ions but also cross-linking takes place.

All gels which are produced by diffusion of polybasic organic acids show capillaries. Treatment of the sol with a mixture of 0.1 N acetic acid and 0.1% formaldehyde solution (1:1) yields an especially strong membrane which is free of capillaries.

Suitable softeners to be added to the sol before gel formation are, for instance, polydiols and polyvinyl alcohols.

Diffusion of the gel-forming ions may be accelerated by gently shaking or vibrating the mold in the ion-supplying solution or by gently stirring the gel-forming solution.

EXAMPLE 22

The gel obtained according to the preceding examples is washed with distilled water and then immersed into a 40% formaldehyde solution for 24 hours. Thereafter the gel is immersed into a solution of 100 parts by weight of 40% formaldehyde and 40 parts by weight of urea which has been buffered to a pH of 7.0 to 8.0. The thus treated gel is heated to remove excess solution and to cause polycondensation to urea-formaldehyde resin which imparts increased stability and strength properties to the resulting bone and tooth matrix.

EXAMPLE 23

The gel obtained according to the preceding Examples 1 to 21 is impregnated with an aqueous 5% mucochloric acid solution, ($\alpha,\beta$-dichloro-$\beta$-formyl acrylic acid). Excess solution is removed. The impregnated gel with substantially open pores is heated at 30° C. for about 5 hours. Thereby, polymerization is effected and the strength properties of the gel are considerably improved.

EXAMPLE 24

The gel obtained according to the preceding Example 1 to 21 is impregnated with an aqueous 10% ethylene glycol diglycidol ether solution (ethylene glycol di-(2,3-epoxy-1-propanol) ether). Excess solution is removed. The impregnated gel with substantially open pores is heated at 40° C. for 20 hours. Thereby polycondensation is effected and the strength properties of the gel are considerably improved.

As stated above, cross-linking and thus improvement of the strength properties of the resulting gel is also achieved by replacing the polymerizable monomers used in Examples 22 to 24 by glutar dialdehyde, 1,4-dibromo butene-(2), 1,4-dichloro butene-(2), butadiene diepoxide, hexamethylene diisocyanate, phenylene diisocyanate, naphthylene diisocyanate, and other substantially physiologically inert, polymerizable monomers which cause cross-linking of the collagen molecules.

EXAMPLE 25

Remineralization is effected by immersing the gel into an aqueous saturated calcium bicarbonate solution, removing the gel from said solution, washing out excess calcium ions, and immersing the calcium ion-impregnated gel into a dilute phosphoric acid solution saturated with dicalcium phosphate ($CaHPO_4$). On repeating said impregnation with saturated calcium bicarbonate solution and phosphoric acid solution several times, hydroxy apatite is incorporated into the ionotropic gel. On repeating, for instance, four times such mineralization, the resulting bone or tooth matrix is mineralized to between 30% and 40%. It is, of course, possible to achieve any degree of mineralization.

It may be pointed out that the addition of mucopolysaccharides or polyuronic acids to the protein sol before gellation is of considerable importance with respect to the formation of the desired ionotropic structure of the gel. Pure protein sols yield only slightly ionotropic gels. But even small amounts of mucopolysaccharides produce pronounced ionotropic effects. Thus, for instance, addition of chondroitin sulfuric acid causes extensive formation of capillaries while hyaluronic acid is more particularly responsible for spatial cross-linking. Addition of these mucopolysaccharides results in strong orientation which is characterized by the birefrigence of the gel.

EXAMPLE 26

The following test were carried out in order to determine the compatibility of the reconstituted bone and tooth material according to the present invention. The material was prepared by removing cattle teeth from freshly slaughtered cattle jaws, cleaning said teeth, comminuting them to small pieces, and demineralizing them in a mixture of 5 N lactic acid and citric acid (1:1) at room temperature for 70 days. The resulting dentine collagen matrix is then washed with distilled water for 7 days by repeatedly replacing the wash water by fresh water. After the matrix has attained a neutral pH-value, it is stored in a mixture of glycerol and water (1:1) at 7° C.

The dentine collagen matrix is then swollen by treating it with 2 N sodium hydroxide solution at 15° C. whereby the sodium hydroxide solution is repeatedly decanted and replaced by fresh solution. The swollen matrix particles are dissolved to a colloidal sol by stirring the particles with 5 parts of 2 N sodium hydroxide solution at 15° C. Said sol has a dry solid content of 1.97%. The symplex sol with collagen is then prepared by adding to the sol an aqueous 4% sodium alginate solution in an amount corresponding to 35.5% of dry solids content in the symplex. The sol is stored at 7° C. for about 50 days and is ionotropically reconstructed by allowing 4 N citric acid to diffuse into the sol placed in a porous mold. The resulting gel is then adjusted to a neutral pH-value by washing with distilled water. It is broken up to pieces of about 10 mm. diameter which are implanted into the gluteal muscles of the sacral region of albino rabbits of 3.5 kg. average body weight. After one week no macroscopic changes such as irritation, hyperemia, hemorrhagia, edema, pus, cyst formation, are observed in the implantation region. After two weeks the gel is completely absorbed. No foreign body cells can be observed on microscopic examination of the region of implantation. These tests prove that the reconstituted gel according to the present invention is completely absorbed by the body and is gradually replaced by body tissue.

The term "bone material" as used hereinabove and in the claims attached hereto designates not only material derived from animal bones but also material derived from animal teeth. Of course, if required, such material may also be derived from human bones and teeth.

Implantation of partly or completely remineralized gel into the animal body, for instance, to replace destroyed bone sections which were removed before implantation, showed that, after about two weeks, the gel has completely replaced the destroyed bone sections so as to reconstitute the removed part of the bone.

When placing the partly remineralized gel obtained from tooth into teeth cavities and covering the fillings with a plastic protective coating, it was found that, after two weeks, the filling has completely filled the cavity.

The same results were achieved in humans whereby bone sections were replaced and cavities in teeth were filled by the partly mineralized gel according to the present invention.

We claim:

1. In a process of degrading and reconstituting bones or teeth, the steps which comprise
   (a) treating ground bones or teeth with an aqueous solution of an effective amount of an agent causing substantially complete demineralization thereof without substantially affecting collagen;
   (b) treating the resulting demineralized collagen-containing bone or tooth material with a swelling agent not substantially affecting collagen to cause swelling of said demineralized collagen-containing bone or tooth material;
   (c) removing the mucopolysaccharides foreign to and incompatible with the human body from said swollen collagen-containing bone or tooth material;
   (d) dissolving the swollen demineralized and mucopolysaccharide-free, collagen-containing bone or tooth material in a solvent for said swollen bone or tooth material to form a colloidal solution;
   (e) adding to said colloidal solution an agent causing orientation of the collagen molecules on subsequent gel formation, said agent being selected from the group consisting of a substantially physiologically inert mucopolysaccharide and a substantially physiologically inert polyuronic acid in an amount sufficient to cause such orientation; and
   (f) causing ions selected from the group consisting of hydrogen ions and polyvalent metal ions to diffuse into said colloidal solution to form a gel of oriented filiform collagen molecules with capillaries extended therethrough.

2. The process of claim 1, wherein in step
   (a) the agent causing demineralization of the ground bones or teeth is an acid forming a water-soluble complex compound with the calcium of the bones or teeth; in step
   (b) the swelling agent is an aqueous solution of an alkali metal hydroxide selected from the group consisting of sodium hydroxide and lithium hydroxide; in step
   (d) the dissolving agent is an aqueous solution of the alkali metal hydroxide as used in step (b), dissolution of the swollen demineralized collagen-containing bone or tooth material being effected by stirring; in step
   (e) the mucopolysaccharide added to the colloidal solution is a mucopolysaccharide selected from the group consisting of alginic acid, chondroitin sulfuric acid, hyaluronic acid, and their water-soluble salts; and in step
   (f) the ions diffusing into the colloidal solution to form a gel therefrom are ions supplied by an electrolyte selected from the group consisting of a dilute aqueous solution of an organic acid and of a dilute aqueous solution of a water-soluble metal salt selected from the group consisting of a water-soluble copper, cadmium, calcium, aluminum, and lanthanum salt.

3. The process of claim 2, wherein in step
   (a) the agent causing demineralization of the ground bones or teeth is an acid selected from the group consisting of citric acid, lactic acid, and hypophosphorous acid; and in step
   (f) the dilute aqueous solution of an organic acid supplying hydrogen ions to cause gel formation is an acid selected from the group consisting of lactic acid and citric acid.

4. The process of claim 1, wherein in step
   (a) the ground bones or teeth are suspended in dilute aqueous acid solution and are subjected to electrodialysis against water until substantially completely demineralized.

5. The process of claim 1, additionally comprising the step of
   (g) alternately and repeatedly causing calcium ions and phosphate ions to diffuse into the gel to cause calcium phosphate to crystallize within the capillaries of said gel.

6. The process of claim 1, wherein in step
   (f) the gel-forming ions are diffused into the colloidal solution by placing said solution into a porous mold and immersing the mold in the electrolyte solution supplying the gel-forming ions.

7. The process of claim 1, additionally comprising the steps of
   (h) impregnating the resulting gel of step (f) with a polymerizable monomeric cross-linking agent compatible with said gel, the amount of said polymerizable monomeric cross-linking agent being insufficient to completely fill the capillaries in said gel; and
   (i) polymerizing the cross-linking agent.

8. The process of claim 1, additionally comprising the step of
   (j) treating the resulting gel of step (f) with an agent hardening the gel, said agent being selected from the group consisting of formaldehyde and tannic acid.

9. Regenerated bone or tooth material with oriented filiform collagen molecules and containing a substantially physiologically inert mucopolysaccharide, said bone or tooth material having capillaries arranged therethrough and being obtained according to the process of claim 1.

10. In a process of degrading and reconstituting bones and teeth, the steps which comprise
    (a) treating ground bones or teeth with an aqueous solution of an effective amount of an agent causing substantially complete demineralization thereof without substantially affecting collagen, said agent being selected from the group consisting of citric acid, lactic acid, and hypophosphorous acid;
    (b) treating the resulting demineralized collagen-containing bone or tooth material with a swelling agent not substantially affecting collagen to cause swelling of said demineralized collagen-containing bone or tooth material, said swelling agent being selected from the group consisting of an aqueous sodium hydroxide solution and an aqueous lithium hydroxide solution, thereby dissolving and removing the mucopolysaccharides from the swollen bone or tooth material;
    (c) dissolving the swollen demineralized and substantially mucopolysaccharide-free, collagen-containing bone or tooth material by means of a solvent for said swollen material to form a colloidal solution, said solvent being selected from the group consisting of an aqueous sodium hydroxide solution and an aqueous lithium hydroxide solution;
    (d) dialyzing the resulting colloidal solution against water;
    (e) adding to said colloidal solution an agent causing orientation of the collagen molecules on subsequent gel formation in an amount sufficient to cause such orientation, said agent being selected from the group consisting of alginic acid, chondroitin sulfuric acid, hyaluronic acid, and their water-soluble salts; and
    (f) causing ions selected from the group consisting of hydrogen ions and polyvalent metal ions to diffuse into said colloidal solution to form a gel of oriented filiform collagen molecules with capillaries extending therethrough, said ions being supplied by an electrolyte selected from the group consisting of a dilute aqueous solution of an acid selected from the group of lactic acid and citric acid and of an aqueous solution of a metal salt selected from the group consisting of copper nitrate, cadmium nitrate, calcium nitrate, aluminum nitrate, and lanthanum nitrate.

11. The process of claim 10, additionally comprising the step of
    (g) treating the resulting gel with a solution of a soluble calcium salt and subsequently with a solution of a water-soluble phosphate and repeating such treatment to cause calcium phosphate to precipitate and crystallize within the capillaries of said gel.

* * * * *